US00PP08894P

United States Patent [19]

Klemm

[11] Patent Number: Plant 8,894

[45] Date of Patent: Sep. 13, 1994

[54] GERANIUM NAMED KLEGAL

[75] Inventor: Siegfried Klemm, Stuttgart, Fed. Rep. of Germany

[73] Assignee: Klemm & Sohn, Stuttgart-Muhlhausen, Fed. Rep. of Germany

[21] Appl. No.: 173,410

[22] Filed: Dec. 23, 1993

[51] Int. Cl.[5] ..... A01H 5/00

[52] U.S. Cl. ..... Plt./87.12

[58] Field of Search ..... Plt. 87.12

*Primary Examiner*—James R. Feyrer

*Attorney, Agent, or Firm*—Tilton, Fallon, Lungmus & Chestnut

[57] ABSTRACT

A new geranium cultivar particularly distinguished by its compact and bushy growth and its cluster stem carrying a large white cluster of florets above strong dark green foliage.

1 Drawing Sheet

BACKGROUND OF THE NEW PLANT

The present invention comprises a new and distinct cultivar of geranium, botanically known as *Pelargonium zonale*-Hybride. The new cultivar is propagated from cuttings resulting from the cross of E 11 and PAC Penja. E 11 is a seedling selected from the E-Generation of our planned breeding program and is not commercially available. E 11 has a white flower color, medium to early precocity and medium floral richness. PAC Penja has a white flower, sometimes a little pink after a cool night, very early precocity, and is very floriferous. Because PAC Penja appears so early there is no time for much vegetative growth. For this reason, the plant stays small. PAC Penja is covered with buds and rather small clusters, but nonetheless the plant appears weak. The foliage is small and light green. PAC Penja has been commercially available through PAC Elsner in Dresden. PAC Penja is also known as PAC "Jade." As a result of this cross the present cultivar was created in 1989 in Stuttgart, Germany and has been repeatedly asexually reproduced by cuttings in Stuttgart, Germany, and Teneriffe, Italy, over a four year period. It has been found to retain its distinctive characteristics through successive propagations; and this novelty appears to be firmly fixed.

The new cultivar is distinguished from other white varieties by its very pure white petal color and dark leaves, precocity, floral richness, continuous flowering, nonshattering flowers, and good suitability for all climates.

DESCRIPTION OF THE DRAWING

This new geranium plant is illustrated by the accompaying photographic drawing which shows blooms, buds, and foliage of the plant in full color, the color shown being as true as can be reasonably obtained by conventinal photographic procedures.

DESCRIPTION OF THE NEW CULTIVAR

The following detailed descriptions set forth the distinctive characteristics of this new geranium. The data which defines these characteristics was collected from asexual reproductions carried out in Stuttgart, Germany. The plant history was taken on 10 week old plants, blossomed under natural light in a greenhouse. Color readings were taken in the greenhouse under ambient light. Color references are primarily to The R.H.S. Colour Chart of The Royal Horticultural Society of London.

THE PLANT

Classification:

*Botanical.*—*Pelargonium zonale*-Hybride.

*Commercial.*—Zonal geranium.

Parentage:

*Seed parent.*—E 11 a seedling from our E-generation of plants.

*Pollen parent.*—PAC Penja (Also known as PAC "Jade").

Form: Compact bush with a high center.

Height of plant: 160–180 mm after 10 weeks.

Stem length: 170–220 mm in June and 290–320 mm in September.

Number of stems per stalk: 9 (in early July).

Number of stalks per plant: 9 (in early July).

Internode length: About 5–12 mm depending on the light where the plant is propagated and the method of propagation.

Growth rate: If propagated in January the blooms can be sold in April, without pinching.

Strength: Good cutting producer for propagation, and the plant performs very well after shipping as a rooted or unrooted cutting.

Foliage:

*Quantity.*—Many leaves.

*Size.*—60×70 mm.

*Shape.*—Round.

*Margin.*—Bicrenate.

*Texture.*—Smooth.

Ribs and veins: None.

Color: Upper side: RHS 147-A and darker, center is a little lighter.

Under side: Green RHS 148-B.

Length of leaf stem: About 55–60 mm.

THE BUD

Size:

*Diameter.*—About 9 mm.

*Length.*—About 1.4 mm.

Shape: Elliptical.

Form: Pointed.

Rate of opening: Medium.

Color: Of petals when sepals first divide: white — 155-C RHS. When petals begin to unfurl: white-RHS 155-B.

Sepals:

*Number.*—5.
*Shape.*—Long and pointed.
*Color.*—Inside — RHS 144-A. Outside — light green-RHS 144-A.
*Form.*—Standing up.

Petiole of floret:
*Length.*—About 24 mm.
*Strength.*—Erectly arranged hemispherically around the end of the cluster stalk.
*Color.*—Green — RHS-144A.

THE FLOWER

Blooming habit: Klegal blooms in April and then continuously and very profusely until the frost. The cluster lasts rather long on the plant. The number of florets per plant varied from 346 to 532 on 3 plants in trials from middle of May to September.

Size of floret: Approximately 47 mm in diameter and 4 mm in depth.

Borne: In a cluster having between about 78–91 florets per cluster.

Shape: When the bloom first opens the blooms are cup-shaped. The blooms change very little, except they become more flat.

Petals:
*Number.*—About six to seven per flower (floret).
*Arrangement.*—Imbricated.
*Form.*—Broad.
*Color.*—Outer petal, body white — RHS 155-D, base a little lighter. Inside petal, body white — RHS 155-D, base a little lighter. Reverse side: white — RHS 155-D.

Texture: Soft.

Appearance: Satiny.

How long do petals remain on stem: About five days depending on weather.

Petaloids:
*Number.*—About 2 to 4.

*Size.*—About 3 to 5 mm.
*Color.*—White — RHS 155-D.

Cluster stem:
*Length.*—90–110 mm.
*Color.*—RHS 137-C.
*Characteristics.*—Upright.

Persistence: Matured florets or clusters should be picked off.

Disease resistance: The present cultivar does not suffer from Botrytis.

Weather resistance: The present cultivar is not unusually affected by wet or hot weather.

Lasting quality:
*On the plant.*—About 27 days.
*As a cut flower.*—About 6–7 days.

Fragrance: No perceptible fragrance.

REPRODUCTIVE ORGANS

Stamens:
*Anthers.*—Seven positioned around the ovaries with 2 mm length.
*Filaments.*—6 mm in length and white.

Pollen: Yellow-orange in color.

Pistils:
*Number.*—One.
*Length of style.*—Approximately 9–11 mm.
*Stigmas.*—White in color.

Ovaries: Green in color.

Seed: Fertile.
*Shape.*—Ovoid.
*Color at maturity.*—RHS 175-B.

I claim:

1. A new and distinct geranium cultivar substantially as herein shown and described, particularly distinguished by its compact and bushy growth and its short cluster stem carrying a large white cluster of florets above strong dark green foliage.

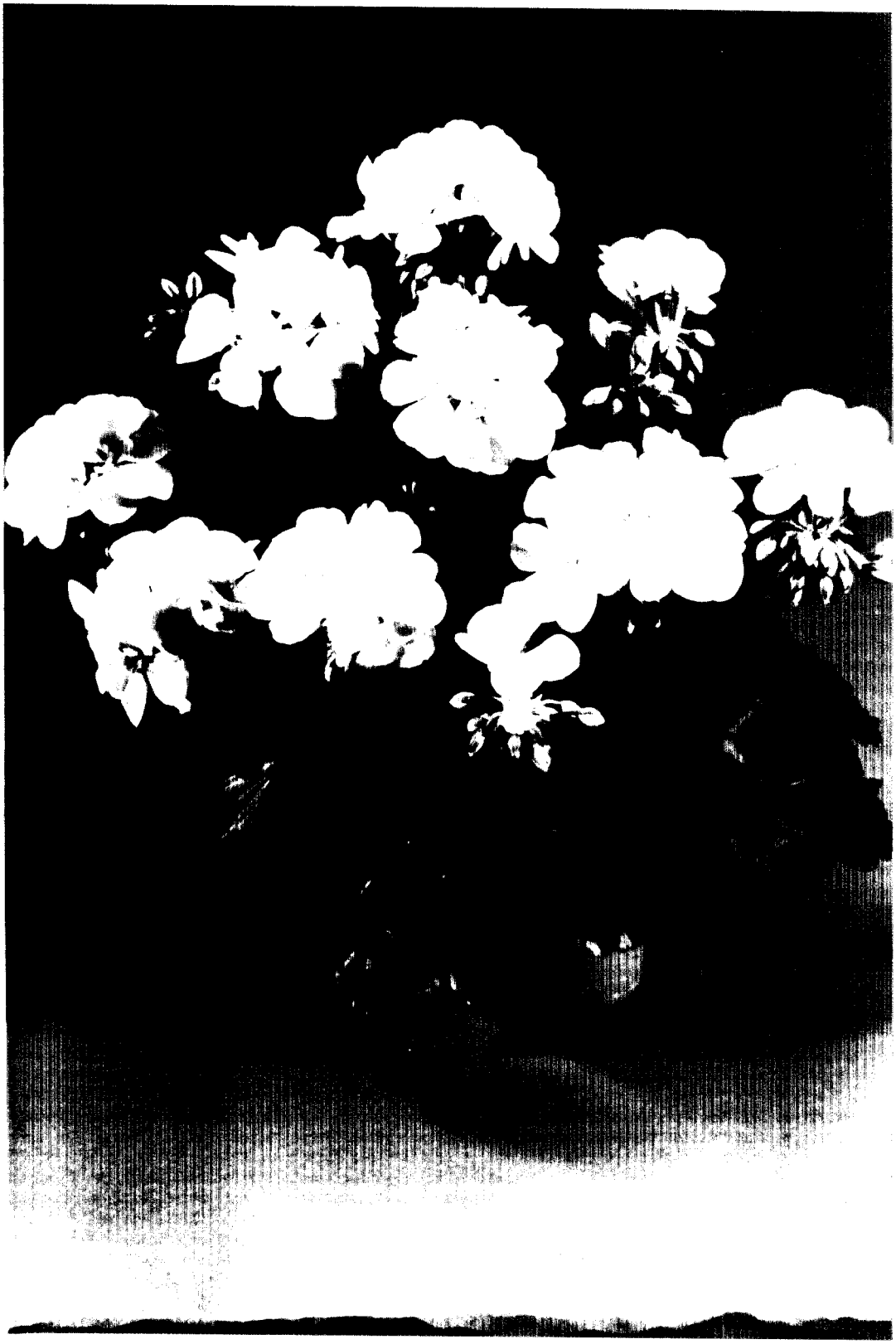

* * * * *